(12) United States Patent
Kim et al.

(10) Patent No.: US 10,682,366 B2
(45) Date of Patent: Jun. 16, 2020

(54) METHOD FOR ENHANCING IMMUNITY USING GINSENOSIDE F1 AS AN ACTIVE INGREDIENT

(71) Applicant: INTELLIGENT SYNTHETIC BIOLOGY CENTER, Daejeon (KR)

(72) Inventors: Sun Chang Kim, Daejeon (KR); Hun Sik Kim, Seoul (KR)

(73) Assignee: INTELLIGENT SYNTHETIC BIOLOGY CENTER, Daejeon (KR)

( * ) Notice: Subject to any disclaimer, the term of this patent is extended or adjusted under 35 U.S.C. 154(b) by 432 days.

(21) Appl. No.: 15/461,722

(22) Filed: Mar. 17, 2017

(65) Prior Publication Data
US 2017/0368084 A1    Dec. 28, 2017

(30) Foreign Application Priority Data

Jun. 22, 2016 (KR) .................. 10-2016-0078028

(51) Int. Cl.
| | | |
|---|---|---|
| *A61K 36/25* | (2006.01) | |
| *A61K 31/704* | (2006.01) | |
| *A61K 31/7032* | (2006.01) | |
| *A23L 33/105* | (2016.01) | |
| *C07K 14/47* | (2006.01) | |
| *C12N 9/64* | (2006.01) | |

(52) U.S. Cl.
CPC .......... *A61K 31/704* (2013.01); *A23L 33/105* (2016.08); *A61K 31/7032* (2013.01); *C07K 14/47* (2013.01); *C12N 9/6467* (2013.01); *C12Y 304/21079* (2013.01)

(58) Field of Classification Search
None
See application file for complete search history.

(56) References Cited

U.S. PATENT DOCUMENTS

| | | | | |
|---|---|---|---|---|
| 2004/0109904 A1* | 6/2004 | Li | ................. | A61K 36/076 424/725 |
| 2018/0071327 A1* | 3/2018 | Kim | ................. | A61K 45/06 |
| 2018/0228823 A1* | 8/2018 | Kim | ................. | A23K 20/163 |

FOREIGN PATENT DOCUMENTS

| | | |
|---|---|---|
| CA | 653 085 | 11/2007 |
| CN | 101965513 | 2/2011 |
| CN | 104288111 A | 1/2015 |
| JP | 2016-88845 A | 5/2016 |
| KR | 10-2004-0087407 | 10/2004 |
| KR | 10-2014-0093305 | 7/2014 |
| KR | 10-2014-0137101 | 12/2014 |
| KR | 10-2014-0148087 | 12/2014 |
| KR | 10-2015-0011576 | 2/2015 |
| KR | 10-2015-0034444 | 4/2015 |
| KR | 2015/080206 | * 7/2015 |
| KR | 2015/094176 | * 8/2015 |
| WO | WO 2016/034100 | 3/2016 |
| WO | WO 2016/178510 | 11/2016 |

OTHER PUBLICATIONS

Kim J. et al. Bioconversion of Major Ginsenosides Rg1 to Minor Ginsenoside F1 Using Novel Recombinant Ginsenoside Hydrolyzing Glycosidase Cloned From . . . J of Biotechnology 161(3)294-301 Jul. 2012. (Year: 2012).*
Derwent Abstract for KR 2015 094176 (Year: 2015).*
Derwent Abstract for KR 2015 080206 (Year: 2015).*
Lu, Jian-Ming, Qizhi Yao, and Changyi Chen, "Ginseng compounds: an update on their molecular mechanisms and medical applications." *Current vascular pharmacology* 7.3 (2009): 293-302.
European Search Report issued in European Application No. 17161503. 2, dated May 24, 2017.
Yu et al., "Protopanaxatrio-type ginsenosides differentially modulate type 1 and type 2 cytokines production from murine splenocytes", *Planta. Med.*, 71: 202-207, 2005.
Wei, Xiaojie, et al. "Stereospecificity of ginsenoside Rg3 in promotion of the immune response to ovalbumin in mice." *International immunology* 24.7 (2012): 465-471.
Yang, G. Z., and Y. L. Yu. "Effects of ginsenoside on the natural killer cell-interferon-interleukin-2 regulatory network and its tumor inhibiting inhibiting effect." *Journal of traditional Chinese medicine= Chung i tsa chih ying wen pan* 8.2 (1988): 135-140.
Kenarova, Buriana et al. "Immunomodulating activity of ginsenoside Rg1 from Panax ginseng." *The Japanese Journal of Pharmacology* 54.4 (1990): 447-454.
Office Communication issued in Canadian Application No. 2,961,400, dated Mar. 28, 2018.
Zhou, Shari-Shan, et al. "Simultaneous determination of original, degraded ginsenosides and aglycones by ultra high performance liquid chromatography coupled with quadrupole time-of-flight mass spectrometry for quantitative evaluation of Du-Shen-Tang, the decoction of ginseng." *Molecules* 19.4 (2014): 4083-4104.
Office Communication issued in Chinese Application No. 201710153242.8, dated Jun. 28, 2019.

* cited by examiner

*Primary Examiner* — Ralph J Gitomer
(74) *Attorney, Agent, or Firm* — Parker Highlander PLLC

(57) ABSTRACT

The present invention relates to compositions for enhancing innate immunity, comprising ginsenoside F1 as an active ingredient. Specifically, the composition according to the present invention promotes degranulation activity and cell-killing activity of natural killer cells, and increases expressions of cell-killing factors, thereby being effectively used as an innate immunity enhancer.

8 Claims, 8 Drawing Sheets
Specification includes a Sequence Listing.

SEQUENCE LISTING

<160> NUMBER OF SEQ ID NOS: 4

<210> SEQ ID NO 1
<211> LENGTH: 21
<212> TYPE: DNA
<213> ORGANISM: Artificial Sequence
<220> FEATURE:
<223> OTHER INFORMATION: Synthetic primer

<400> SEQUENCE: 1
cgcctacctc aggcttatct c                                      21

<210> SEQ ID NO 2
<211> LENGTH: 19
<212> TYPE: DNA
<213> ORGANISM: Artificial Sequence
<220> FEATURE:
<223> OTHER INFORMATION: Synthetic primer

<400> SEQUENCE: 2
cctcgacagt caggcagtc                                         19

<210> SEQ ID NO 3
<211> LENGTH: 21
<212> TYPE: DNA
<213> ORGANISM: Artificial Sequence
<220> FEATURE:
<223> OTHER INFORMATION: Synthetic primer

```
<400> SEQUENCE: 3
ccctgggaaa acactcacac a                                               21

<210> SEQ ID NO 4
<211> LENGTH: 19
<212> TYPE: DNA
<213> ORGANISM: Artificial Sequence
<220> FEATURE:
<223> OTHER INFORMATION: Synthetic primer

<400> SEQUENCE: 4
cacaactcaa tggtactgt                                                  19
```

METHOD FOR ENHANCING IMMUNITY USING GINSENOSIDE F1 AS AN ACTIVE INGREDIENT

This application claims the benefit of Korean Patent Application No 10-2016-0078028, filed Jun. 22, 2016, the entirety of which is incorporated herein by reference.

BACKGROUND OF THE INVENTION

Field of the Invention

The present invention relates to a pharmaceutical composition for enhancing immunity, including ginsenoside F1 as an active ingredient.

Further, the present invention relates to a food composition for enhancing immunity, including ginsenoside F1 as an active ingredient.

Further, the present invention relates to a method of enhancing immunity, including administering ginsenoside F1 to a subject.

Further, the present invention relates to a composition for producing perforin or granzyme, including ginsenoside F1 and natural killer cells.

Description of the Related Art

Immunity is largely divided into innate immunity that is present at birth and acquired immunity that is acquired by adaptation during life. Here, innate immunity, also called 'natural immunity', provides a non-specific response against pathogens, and has no specific memory function. Actually, such innate immunity defends most infections. In contrast, acquired immunity has a memory function against the re-exposed invading pathogens, and when invasion of the same pathogens occurs again, a specific immune response begins to effectively eliminate the pathogens.

In recent years, there has been a problem that internal factors such as the lack of physical activity, stress, etc. and external factors such as air pollution, etc. act in combination to remarkably lower immunity. Therefore, it is necessary to study substances showing immune enhancing effects, and in particular, the importance of innate immunity broadly involved in defense against most infections is increasing.

Korean Patent Publication No. 10-2015-0011576 discloses a pharmaceutical composition for enhancing immunity, including the root of *Eleutherococcus senticosus* as an active ingredient. Korean Patent Publication No. 10-2014-0148087 discloses an anti-viral composition and enhancing innate immunity, including an extract of *Phellodendron Amurense* bark. Many studies have been actively conducted on immune enhancing compositions including natural substances among a variety of substances.

Meanwhile, ginsenoside is a saponin present in ginseng. There are more than 30 different kinds of ginsenosides, which are divided into PPD (protopanaxadiol)-type and PPT (protopanaxatriol)-type according to their structures. Ginsenosides are known to exhibit different pharmacological activities depending on their chemical structures (*Curr Vasc Pharmacol.* 2009 July; 7(3):293-302). Among the ginsenosides, minor ginsenosides are present in very small amounts in ginseng, and it is difficult to separate minor ginsenosides. Therefore, studies on minor ginsenosides have not been actively conducted vet.

Accordingly, the present inventors have made many efforts to find a compound. having excellent immune enhancing effects. As a result, they found that ginsenoside F1 has excellent immune enhancing effects, in particular, innate immune enhancing effects, compared to other ginsenosides, thereby completing the present invention.

SUMMARY OF THE INVENTION

An object of the present invention is to provide a pharmaceutical composition for enhancing immunity, including ginsenoside F1 as an active ingredient.

Another object of the present invention is to provide a food composition for enhancing immunity, including ginsenoside F1 as an active ingredient.

Still another object of the present invention is to provide a method of enhancing immunity, including administering ginsenoside F1 to a subject.

Still another object of the present invention is to provide a composition for producing perforin or granzyme, including ginsenoside F1 and natural killer cells.

DETAILED DESCRIPTION OF THE PREFERRED EMBODIMENTS

While the present inventors have conducted studies regarding immune enhancement, they pretreated natural killer cells (NK cells) with ginsenoside F1, and then evaluated a target cell-killing, activity of natural killer cells by various methods. As a result, the present inventors found that ginsenoside F1 exhibited an activity superior to other ginsenosides, and therefore, they first demonstrated that a composition including ginsenoside F1 exhibits superior immune enhancing effects.

To achieve the above objects, an aspect of the present invention provides a pharmaceutical composition for enhancing immunity, including ginsenoside F1 as an active ingredient.

The term "ginsenoside F1", as used herein, a kind of saponin which is a major active component of ginseng or red ginseng, refers to ginsenoside belonging to PPT (protopanaxatriol)-type.

The term "immune enhancement", as used herein, refers to enhancement of the bio-defense ability of the body's internal environment against an external factor, pathogens. The immunity may be divided into innate immunity that is present at birth and acquired immunity (adaptive immunity) that is acquired by adaptation. The immunity in the present invention may be innate immunity.

The pharmaceutical composition may enhance activities of innate immune cells.

The innate immune cells may be any one selected from the group consisting of natural killer cells (NK cells), immune cells, peripheral blood mononuclear cells (PBMCs), and dendritic cells, but are not limited thereto. Specifically, the innate immune cells may be natural killer cells.

The pharmaceutical composition may promote degranulation activity of innate immune cells.

The term "degranulation activity", as used herein, refers to an activity to release molecules accumulated in secretory granules. In the present invention, the degranulation activity may be an activity to release molecules accumulated in innate immune cells. The degranulation activity of innate immune cells may be determined by analyzing expression of CD107a which is a marker generally used to evaluate the degranulation activity, but is not limited thereto.

In an embodiment of the present invention, when innate immune cells were pretreated with ginsenoside F1, was confirmed that CD107a expression was increased (FIGS. 2b and 2c), suggesting that ginsenoside F1 may promote the degranulation activity of natural killer cells. In particular, it was confirmed that ginsenoside F1 showed the most excellent effect of promoting the degranulation activity, compared to other ginsenosides.

The pharmaceutical composition may promote a cell-killing activity of natural killer cells.

In an embodiment of the present invention, natural killer cells were pretreated with ginsenoside F1, and their cell-killing, activity was evaluated. As a result, a high level of target cell cytolysis was observed (FIG. 3a). In particular, when primary natural killer cells were pretreated with ginsenoside F1, a high level of target cell cytolysis was also observed (FIG. 4a). Further, when effectiveness of in-vivo target cell-killing activity of ginsenoside F1 was evaluated by examining reduction of natural killer cell-sensitive RMA-S ginsenoside F1 also showed excellent effect of reducing RMA-S cells (FIG. 7).

The pharmaceutical composition may further include ginsenoside Rg3. The ginsenoside Rg3 is a kind of PPD (protopanaxadiol)-type ginsenosides.

In an embodiment of the present invention, natural killer cells were pretreated with ginsenoside Rg3, and their target cell-killing activity was evaluated. As a result, CD107a expression in natural killer cells was increased (FIGS. 2b and 2c), and a high level of target cell cytolysis was observed (FIG. 3b). In particular, when primary natural killer cells were pretreated with ginsenoside Rg3, a high level of target cell cytolysis was also observed (FIG. 4b). Therefore, it can be seen that the pharmaceutical composition of the present invention may further include ginsenoside Rg3 having an immune-enhancing activity.

The pharmaceutical composition may include ginsenoside F1 and ginsenoside Rg3 at a weight ratio of 1:0.1 to 1:1.

When the weight ratio of ginsenoside F1 and ginsenoside Rg3 is below 1:0.1, the immune enhancing effect of ginsenoside Rg3 hardly occurs, and when the weight ratio of ginsenoside F1 and ginsenoside Rg3 is above 1:1, a synergistic effect of immune enhancement b mixing may be not satisfactory.

The pharmaceutical composition may increase expressions of cell-killing factors of natural killer cells.

The term "cell-killing factor", as used herein, refers to a substance showing a cell-killing activity, and in the present invention, the cell-killing factor refers to a substance showing the cell-killing activity, which is released from natural killer cells, and specifically, it may be perforin or granzyme, but is not limited thereto.

In an embodiment of the present invention, when natural killer cells were pretreated with ginsenoside F1, perforin and granzyme B expressions were found to be increased (FIGS. 6a and 6b), suggesting that ginsenoside F1 increases expressions of cell-killing factors of natural killer cells.

The pharmaceutical composition may include a pharmaceutically acceptable carrier. The "pharmaceutically acceptable carrier" refers to a carrier, an excipient, or a diluent that does not cause significant irritation to an organism and does not abrogate the biological activity and properties of the administered compound. Specifically, it may be a non-naturally occurring carrier. A kind of the carrier usable in the present invention is not particularly limited, and any carrier may be used as long as it is generally used in the art and is pharmaceutically acceptable. Non-limiting examples of the carrier may include normal saline, sterile water, Ringer's solution, buffered saline, an albumin injection solution, a dextrose solution, a maltodextrin solution, glycerol, ethanol, etc. These may be used alone or in a mixture of two or more thereof.

The composition including the pharmaceutically acceptable carrier may be prepared in a variety of formulations for oral or parenteral administration. Formulations may be prepared using diluents or excipients ordinarily employed, such as a tiller, an extender, a binder, a wetting agent, a disintegrating agent, a surfactant, etc.

In detail, solid formulations for oral administration may include a tablet, a pill, a powder, a granule, a capsule, etc., and the solid preparation may be prepared by mixing the compound with at least one excipient such as starch, calcium carbonate, sucrose, lactose, gelatin, etc. Further, in addition to simple excipients, lubricants such as magnesium stearate, talc, etc. may be used. Liquid formulations for oral administration may include a suspension, a liquid for internal use, an emulsion, a syrup, etc., and may include various excipients, for example, a wetting agent, a flavoring agent, an aromatic, a preservative, etc., in addition to water and liquid paraffin, which are frequently used simple diluents. Formulations for parenteral administration may include a sterilized. aqueous solution, a non-aqueous solvent, a suspending agent, an emulsion, a lyophilized preparation, and a suppository. As the non-aqueous solvent or suspending agent, propylene glycol, polyethylene glycol, plant oils such as olive oil, injectable esters such as ethyl oleate, etc. may be used. As a base of the suppository, witepsol, Macrogol, Tween 61, cacao butter, laurin butter, glycerogelatin, etc. may be used.

Further, the pharmaceutical composition of the present invention may include a pharmaceutically effective amount of ginsenoside F1. The term "pharmaceutically effective amount", as used herein, refers to an amount sufficient to treat diseases, at a reasonable benefit/risk ratio applicable to any medical treatment. Generally, the pharmaceutical composition of the present invention may be administered in an amount of 0.001 mg/kg to 1000 mg/kg, specifically 0.05 mg/kg to 200 mg/kg, and more specifically 0.1 mg/kg to 100 mg/kg once or divided into several times per day. However, with respect to the objects of the present invention, the specific therapeutically effective dose level for any particular patient may vary depending on a variety of factors such as the type and degree of the response to be achieved, the specific composition, including whether another agent, if any, is employed, the age, body weight, general health conditions, sex and diet of the patient, administration time, administration route, and excretion rate of the composition, treatment period, drugs used in combination or coincidental with the specific composition, and similar factors well known in the medical arts.

The pharmaceutical composition of the present invention may be used as an immune enhancer, an adjuvant additive capable of improving vaccine efficacy, an auxiliary therapeutic agent (e.g., auxiliary anti-cancer agent) capable of enhancing therapeutic efficacy, etc.

Another aspect of the present invention provides a food composition for enhancing innate immunity, including ginsenoside F1 as an active ingredient.

The terms "ginsenoside F1" and "immune enhancement" are the same as described above.

The term "food", as used herein, may include meat, sausage, bread, chocolate, candy, snack, cookie, pizza, instant noodle, other noodles, chewing gum, dairy products including ice cream, various kinds of soup, beverage, tea, drink, alcoholic beverages, vitamin complex, health functional food, and health foods, etc., and includes all kinds of common foods.

The term "health functional food" is the same term as food for special health use (FOSHU), and refers to a food having high medicinal and medical effects, which is processed to effectively exert a body-regulating function and to supply nutrients. The term "functional", as used herein, means that it is taken for the purpose of controlling nutrients with respect to structures and functions of the human body or of obtaining effects beneficial for health care, such as physiological effects. The food of the present invention may be prepared by a method commonly used in the art, and it may also be prepared by adding raw materials and ingredients which are generally added in the art during the preparation. The food may also be prepared in any formulation without limitation, as long as it is acceptable as a food. The food composition of the present invention may be prepared in a variety of formulations, and unlike other common drugs, the food composition may be prepared by using foods as raw materials, and thus it has an advantage of avoiding side effects associated with long-term administration of drugs, and it may be very portable. Therefore, the food of the present invention is ingestible as a supplement for improving immune enhancing effects.

The term "health food" refers to a food that positively maintains or improves health compared to general foods, and the term "health supplement food" refers to a food to be used as a health supplement. In some cases, the terms "health functional food", "health food" and "health supplement food" are used interchangeably with each other.

Specifically, the health functional food may be a food prepared by adding ginsenoside F1 to food materials such as beverages, teas, flavors, gum, snacks, etc., or prepared as a capsule, powder, suspension, etc. When this health functional food is ingested, it brings about a specific effect on health, and unlike other common drugs, the health functional food composition has an advantage of avoiding side effects associated with long-term administration of drugs, because of being prepared by using foods as raw materials.

Since the food composition of the present invention may be ingested routinely, high immune enhancing effects may be expected, and therefore, it is very useful.

The composition may further include a physiologically acceptable carrier. A kind of the carrier is not particularly limited, and any carrier may be used as long as it is a carrier commonly used in the art.

The composition may further include an additive which is commonly used in food compositions to enhance flavor, taste, color, etc. For example, the composition may include vitamins A, C, D, E, B1, B2, B6, B12, niacin, biotin, folate, pantothenic acid, etc. The composition may also include a mineral, such as zinc(Zn), iron(Fe), calcium(Ca), chromium (Cr), magnesium(Mg), manganese(Mn), copper(Cu), chromium(Cr), etc. The composition may also include an amino acid, such as lysine, tryptophan, cysteine, valine, etc.

The composition may also be supplemented with food additives, including antiseptics (e.g., potassium sorbate, sodium benzoate, salicylic acid, sodium dehydroacetate, etc.), disinfecting agents (e.g., bleaching powder and high-test bleaching powder, sodium hypochlorite, etc.), antioxidants (e.g., butylhydroxyanisole (BHA), butylhydroxytoluene (BHT), etc.), colorants (e.g., tar dye, etc.), color fixing agents (e.g., sodium nitrate, sodium nitrite, etc.), bleaching agents (e.g., sodium sulfite), seasoning agents (e.g., MSG, sodium glutamate, etc.), sweeteners (e.g., dulcin, cyclamate, saccharine, sodium, etc.), flavoring agents (vanillin, lactones, etc.), blowing agents (alum, potassium D-bitartrate, etc.), fortifying agents, emulsifying agents, thickening agents, coating agents, gum bases, antifoaming agents, solvents, improving agents, etc. The additives may be selected according to food type, and they may be used in suitable amounts.

The ginsenoside F1 may be added as it is or together with other foods or food components, and appropriately used according to a common method. A mixed amount of the active ingredients may be suitably determined according to the intended use (preventive, health, or therapeutic purposes). Generally, the food composition of the present invention may be added in an amount of 50 parts by weight or less, and specifically 20 parts by weight of less with respect to a food or drink, upon preparing the food or drink. When consumed for a long period of time for health and sanitary purposes, the composition may be used in an amount below the range. Also, it is apparent that the active ingredients may be used in an amount above the range, because the active ingredient carries no safety risk.

The food composition of the present invention may be used as, for example, a health beverage composition. In this case, the health beverage composition may include various flavoring agents or natural carbohydrates, like common beverages. The above-described natural carbohydrates may include monosaccharides such as glucose and fructose; disaccharides such as maltose and sucrose; polysaccharides such as dextrin and. cyclodextrin; sugar alcohols such as xylitol, sorbitol, erythritol, etc. As a sweetening agent, a natural sweetening agent such as thaumatin or stevia extract; a synthetic sweetening agent such as saccharin and aspartame, etc. may be used. The content of the natural carbohydrate is generally in a range of about 0.01 g to about 0.04 g, specifically about 0.02 g to 0.03 g per 100 mL of the composition of the present invention.

In addition, the health beverage composition may further include various nutritional supplements, vitamins, electrolytes, flavorings, coloring agents, pectic acid and salts thereof, alginic acid and salts thereof, organic acids, protective-colloidal thickeners, pH regulators, stabilizers, preservatives, glycerin, alcohols or carbonating agents, etc. Furthermore, the health beverage composition may include fruit flesh used for natural fruit juices, fruit juice drinks, or vegetable drinks. These components may be used alone or in combination thereof. A ratio of these additives may not be important, but it is generally selected in the range of 0.01 parts by weight to 0.1 parts by weight per 100 parts by weight of the composition of the present invention.

The food composition of the present invention may include ginsenoside F1 in many different ranges of % by weight, as long as the immune-enhancing effects may be obtained. Specifically, ginsenoside F1 may be included in an amount of 0.00001% by weight to 100% by weight, or 0.01% by weight to 80% by weight, based on the total weight of the food composition.

Still another aspect provides a method of enhancing immunity, including administering ginsenoside F1 to a subject.

The terms "ginsenoside F1" and "immune enhancement" are the same as described above.

The term "administering", as used herein, refers to introduction of the composition of the present invention into a subject using any suitable method. The composition may be administered via any of the common routes, as long as it is able to reach the desired tissue. A mode of the administration may include intraperitoneal, intravenous, intramuscular, subcutaneous, intradermal, oral, topical, and intranasal administration, but is not limited thereto.

The term "subject", as used herein, refers to all kinds of animals including rats, mice, or livestock as well as humans who are in need of immune enhancement or have the possibility of needing immune enhancement. Specifically, the subject may be mammals include humans.

The composition may be administered in a pharmaceutically effective amount.

The term "pharmaceutically effective amount", as used herein, refers to an amount sufficient to treat diseases, at a reasonable benefit/risk ratio applicable to any medical treatment. An effective dose level may vary depending on a variety of factors including the type and severity, age, and sex of the subject, drug activity, drug sensitivity, administration time, administration route, excretion rate, treatment period, and co-administered drugs, and other factors well known in the medical field. For example, the pharmaceutical composition including ginsenoside F1 may be administered in an amount of 0.0001 mg/kg to 1000 mg/kg, and specifically, 0.001 mg/kg to 100 mg/kg per day.

The pharmaceutical composition of the present invention may be administered every day or intermittently. Administration may be performed once or divided into several times per day. Further, the pharmaceutical composition of the present invention may be used singly or in combination with other therapeutic agents in order to enhance immunity. Taking all factors into consideration, it is important to conduct administration of minimal doses capable of giving the greatest effects with no adverse effects, such doses being readily determined by those skilled in the art.

Still another aspect of the present invention provides a composition for producing perforin or granzyme, including ginsenoside F1 and natural killer cells.

The terms "ginsenoside F1" and "natural killer cell" are the same as described above.

In an embodiment of the present invention, when natural killer cells were pretreated with ginsenoside F1, perforin and granzyme B expressions were found to be increased (FIGS. 6a and 6b), suggesting that the composition including ginsenoside F1 and natural killer cells produces perforin or granzyme.

Effect of the Invention

A composition according to the present invention promotes degranulation activity and cell-killing activity of natural killer cells, and increases expressions of cell-killing factors, thereby being effectively used as an immune enhancer.

DETAILED DESCRIPTION OF THE INVENTION

Hereinafter, the constitution and effects of the present invention will be described in more detail with reference to Examples. However, these Examples are for illustrative purposes only, and the invention is not intended to be limited by these Examples.

EXAMPLE 1

Effect of Ginsenoside F1 on Degranulation Activity of Innate Immune Cells

Effect of ginsenoside F1 on degranulation activity of innate immune cells was measured by fluorescence activated cell sorter (FACS).

Figure 1:
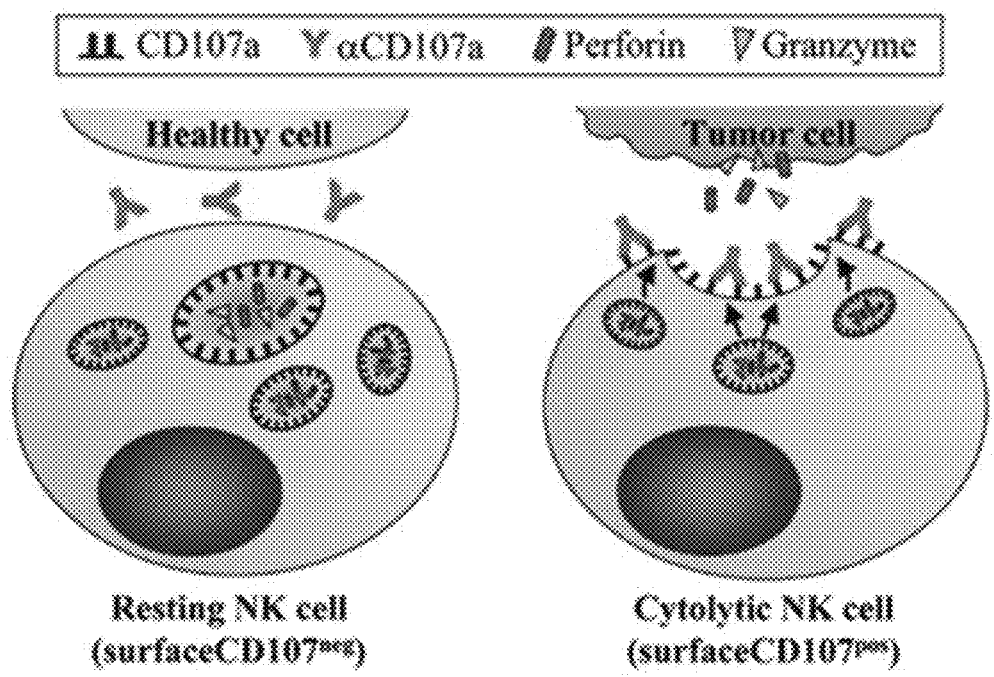
FIG. 1 is a schematic illustration showing a degranulation phenomenon of natural killer cells.

In detail, peripheral blood mononuclear cells (PBMCs) separated from the blood and purified natural killer cells were pretreated with ginsenoside, and then co-cultured with K562 cell or 721.221 cell which is a target cell of the above cells, respectively. Thereafter, the surfaces of the peripheral blood mononuclear cells and the natural killer cells were stained with fluorochrome-conjugated anti-CD3, anti-CD56, and anti-CD107a antibodies. Meanwhile, degranulation activity of peripheral blood mononuclear cells or natural killer cells is proportional to CD107a expression on cell surface, as shown in FIG. 1. Therefore, CD107a expression levels of the peripheral blood mononuclear cells and the natural killer cells were measured by a FACS machine.

Figure 2A:
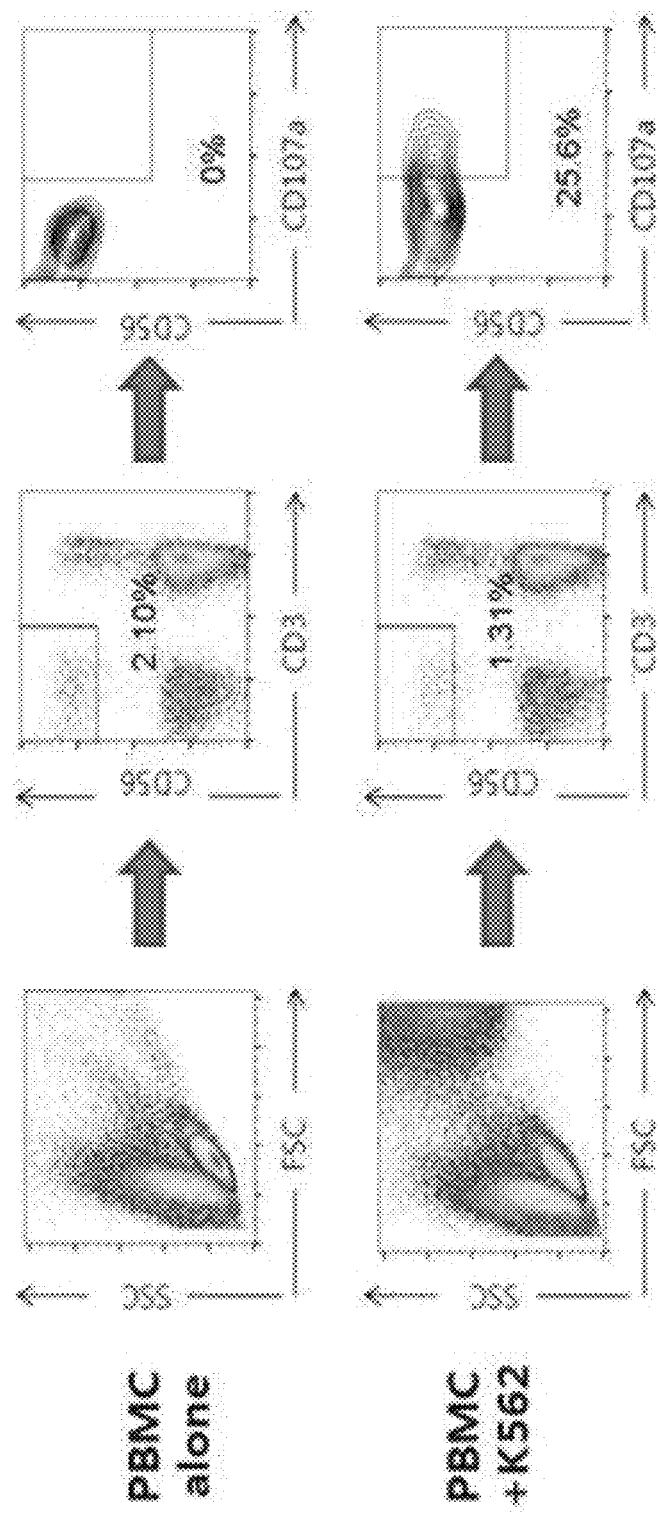
FIG. 2a is a graph showing a comparison of CD107a expression levels in peripheral blood mononuclear cells (PBMCs) cultured without a target cell or co-cultured with the target cell.

As a result, the peripheral blood mononuclear cells cultured without the target cell showed little CD107a expression, whereas the peripheral blood mononuclear cells co-cultured with the target cell showed CD107a expression (FIG. 2a). Further, ginsenoside-treated groups showed CD107a overexpression, compared to a DMSO (vehicle)-treated group, even though co-cultured with the target cells (FIG. 2b).

Figure 2B:
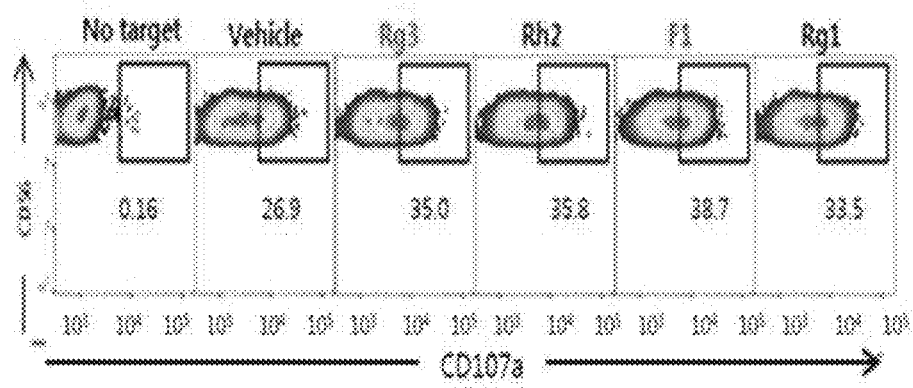
FIG. 2b is a graph showing CD107a expression in peripheral blood mononuclear cells (PBMCs) treated with ginsenoside Rg3, Rh2, F1 or Rg1.
Figure 2C:
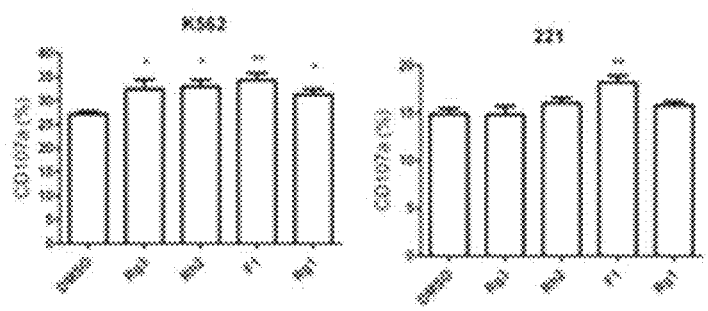
FIG. 2c is a graph showing a comparison of CD107a expression levels in peripheral blood mononuclear cells (PBMCs) treated with ginsenoside Rg3, Rh2, F1 or Rg1.

Specifically, when co-culture was conducted using a chronic myelogenous leukemia cell line, K562 or a human B cell, 721.221 as a target cell, all ginsenoside-treated groups showed increased CD1.07a expression, compared to the DMSO (vehicle)-treated group, and a ginsenoside F1-treated group showed the highest CD107a expression (FIGS. 2b and 2c). Accordingly, it was confirmed that ginsenoside F1 and Rg3 showed excellent, immune-enhancing effects, and in particular, ginsenoside F1 showed the most excellent immune-enhancing effects.

EXAMPLE 2

Effect of Ginsenoside F1 on Cell-Killing Activity of Natural Killer Cells

In order to examine whether ginsenoside F1 increases cell-killing activity of natural killer cells, cytolysis of target cells was measured.

In detail, peripheral blood mononuclear cells (PBMCs) separated from the blood and purified natural killer cells were pretreated with ginsenoside F1 or Rg3, and then co-cultured with K562 cell or 721.221 cell which is an europium-labeled target cells. The natural killer cell and the target cell were mixed at a ratio of 5:1, 10:1, 20:1, and 40:1, followed by culture. Meanwhile, intensity of fluorescence emitted from the target cell is proportional to cell-killing activity of natural killer cell. Therefore, a culture medium was separated by centrifugation, and then fluorescence emitted by cell lysis of the target cell was measured by using a microplate reader.

Figure 3A:
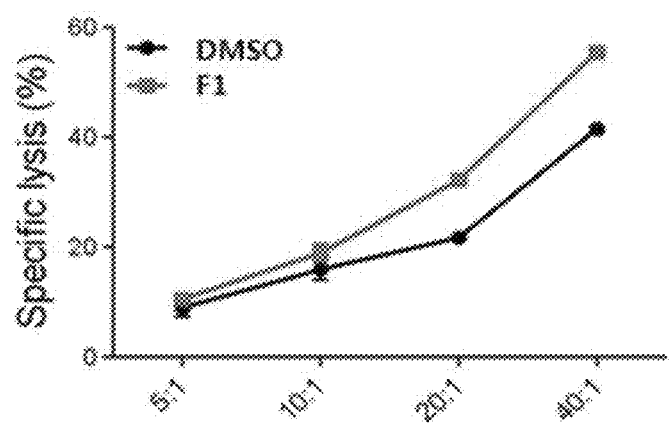
FIG. 3a is a graph showing cytolysis of target cells upon treatment of natural killer cells with ginsenoside F1.
Figure 3B:
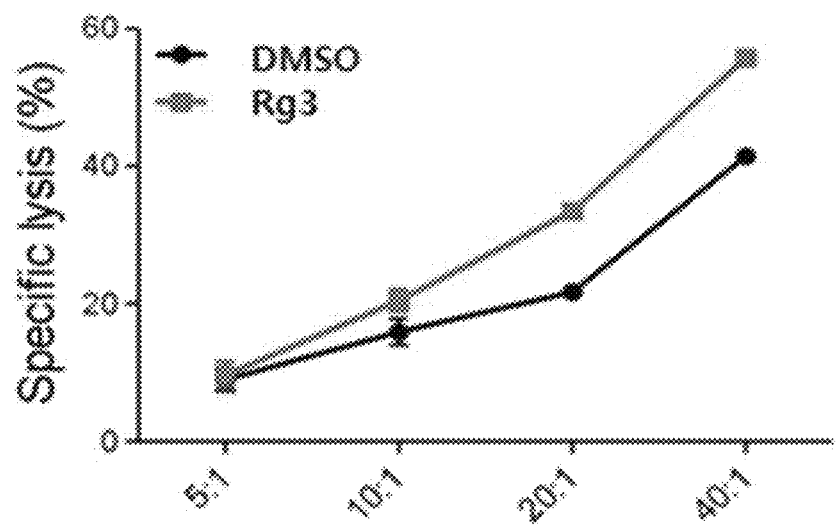
FIG. 3b is a graph showing cytolysis of target cells upon treatment of natural killer cells with ginsenoside Rg3.

As a result, all ginsenoside F1 or Rg3-treated groups at the above culture ratios showed high cytolysis of target cells, compared to a DMSO-treated group (FIGS. 3a and 3b). Accordingly, it was confirmed that ginsenoside F1 and Rg3 increase cell-killing activity of natural killer cells.

EXAMPLE 3

Effect of Ginsenoside F1 on Cell-Killing Activity of Primary Natural Killer Cells

Example 3-1

Separation of Primary Natural Killer Cells

Blood (50 ml) of a healthy donor was collected in a vacutainer cell preparation tube (BD Biosciences) containing sodium heparin. Thereafter, the blood was percoll-gradient centrifuged to recover a buffy coat which is a white thin layer consisted of platelets and white blood cells. Peripheral blood mononuclear cells obtained by washing this buffy coat with PBS were separated by using a human NK cell negative selection kit (Miltenyl Biotech). Part of the separated natural killer cells and a FACS buffer were mixed, and then purity of natural killer cells (CD3$^-$/CD16$^+$) and the number and ratio of CD56$^{dim}$/CD16$^+$, CD56$^{bright}$/CD16$^-$, and CD56$^{bright}$/CD16$^+$ were measured by using a FACS machine and fluorochrome-conjugated anti-CD3, anti-CD56, and anti-CD107a antibodies. Natural killer cells with purity of 95% or more were used in experiments.

Example 3-2

Cell-Killing Activity of Primary Natural Killer Cells

The primary natural killer cells separated by the method of Example 3-1 were used to examine whether ginsenoside F1 increases cell-killing activity of primary natural killer cells, in the same manner as in Example 2.

Figure 4A:
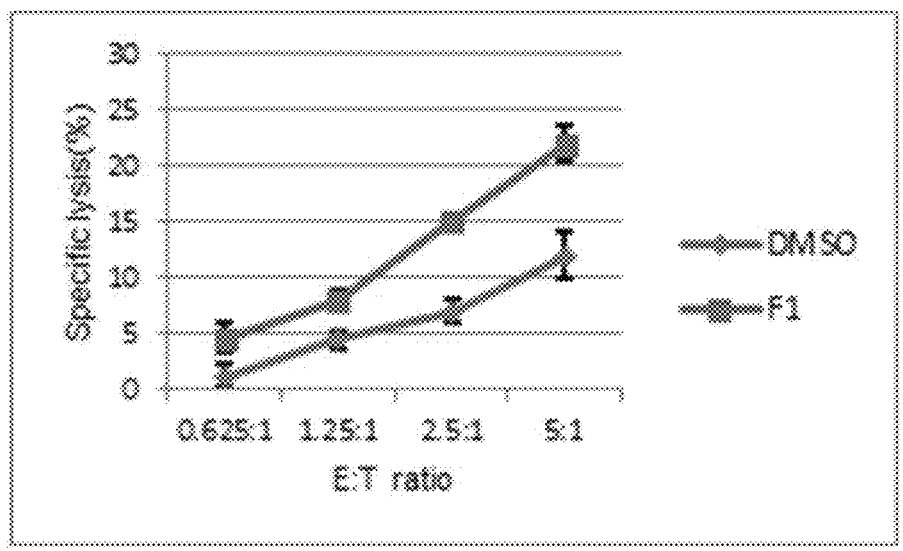
FIG. 4a is a graph showing cytolysis of target cells upon treatment of primary natural killer cells with ginsenoside F1.
Figure 4B:
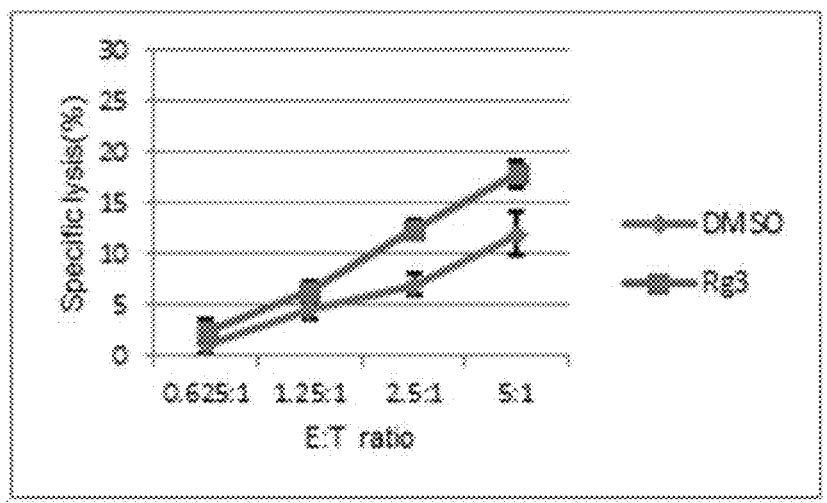
FIG. 4b is a graph showing cytolysis of target cells upon treatment of primary natural killer cells with ginsenoside Rg3.
Figure 4C:
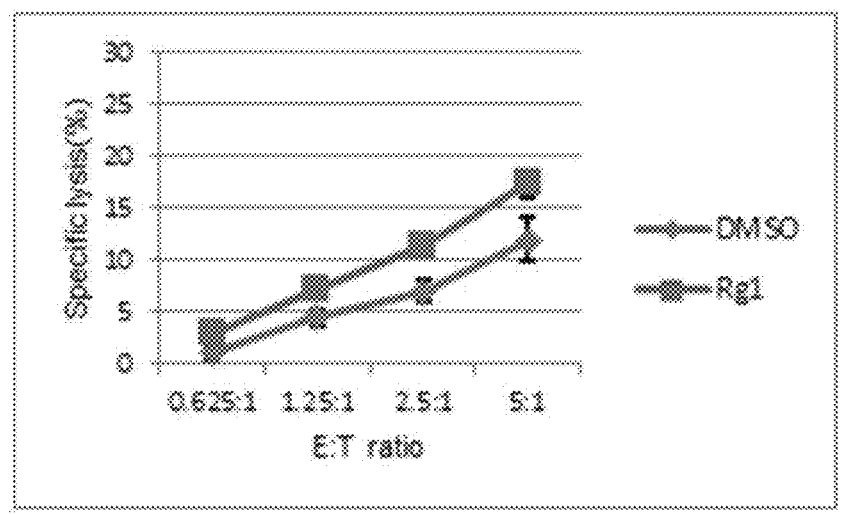
FIG. 4c is a graph showing cytolysis of target cells upon treatment of primary natural killer cells with ginsenoside

As a result, ginsenoside F1, Rg3, and Rg1-treated group showed high cytolysis of target cells, compared to a DMSO-treated group (FIGS. 4a to 4c). In particular, the ginsenoside F1-treated group showed remarkably excellent cytolysis, compared to the ginsenoside Rg3 and Rg1-treated group. Accordingly, it was confirmed that ginsenoside F1 and Rg3 show excellent cell-killing activity of primary natural killer cells, and ginsenoside F1 shows the most excellent effect.

EXAMPLE 4

Calcium Flux Assay by Treatment with Ginsenoside F1

To investigate a natural killer cell-based immune enhancement mechanism of ginsenoside F1 calcium flux assay of individual cells was performed by live cell imaging using confocal microscopy.

In detail, primary natural killer cells were purified (>97%) by the method of Example 3-1, and then treated with ginsenoside F1 or Rg1. For 30 seconds, a basal calcium level was measured, and then natural killer cells were activated using a combination of NKG2D antibody and 2B4 antibody, followed by calcium flux assay by confocal live cell imaging.

Figure 5:
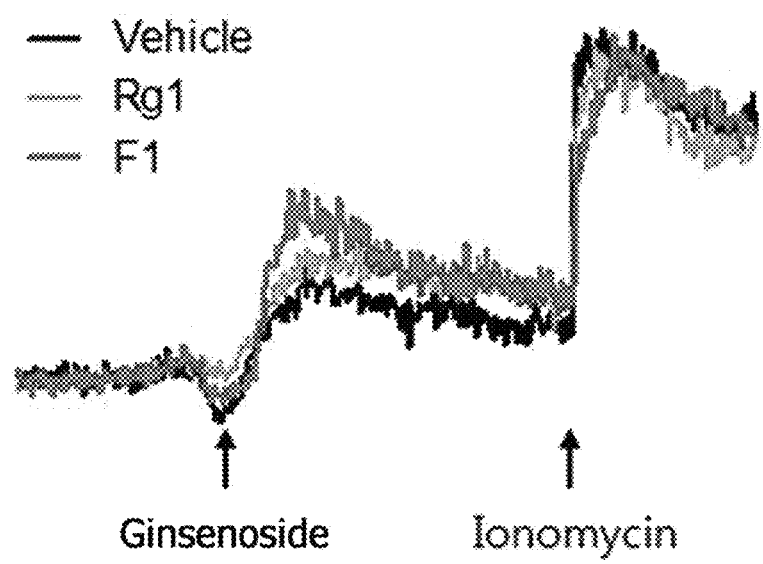
FIG. 5 is a graph showing increased calcium flux in natural killer cells by ginsenoside F1.

As a result, it was confirmed that ginsenoside F1 more effectively promotes calcium flux of natural killer cells, compared to ginsenoside Rg1 (FIG. 5). Accordingly, it was confirmed that ginsenoside F1 exhibits excellent immune-enhancing effects, compared to ginsenoside Rg1.

EXAMPLE 5

Analysis of Cell-Killing Factors

To investigate a cell-killing activation mechanism of natural killer cells by ginsenoside F1, primary natural killer cells purified by the method of Example 3-1 were treated with ginsenoside F1 or Rg1. 12 hours later, total RNA was isolated, and then expressions of perforin and granzyme B which are representative cell-killing factors of natural killer cells were analyzed by quantitative RT-PCR.

In detail, total RNA was isolated from natural killer cells using a TRIzol reagent, and cDNA was synthesized using primers of unknown sequences, which were manufactured by Toyobo, and reverse transcriptase. Thereafter, quantitative RT-PCR was performed using primers of the following Table 1 and SYBR PCR Master Mix (Toyobo).

TABLE 1

| Type of primer | | Nucleotide sequence (5'-3') |
|---|---|---|
| Perforin | Forward | CGCCTACCTCAGGCTTATCTC (SEQ ID NO: 1) |
| | Reverse | CCTCGACAGTCAGGCAGTC (SEQ ID NO: 2) |
| Granzyme B | Forward | CCCTGGGAAAACACTCACACA (SEQ ID NO: 3) |
| | Reverse | CACAACTCAATGGTACTGT (SEQ ID NO: 4) |

PCR conditions are the same as in the following Table 2.

TABLE 2

| PCR conditions | | Temperature (° C.) | Time |
|---|---|---|---|
| 1 cycle | | 95 | 10 min |
| 40 cycle | Denaturation | 95 | 30 sec |
| | Annealing | 60 | 30 sec |
| | Extension | 72 | 30 sec |

Figure 6A:
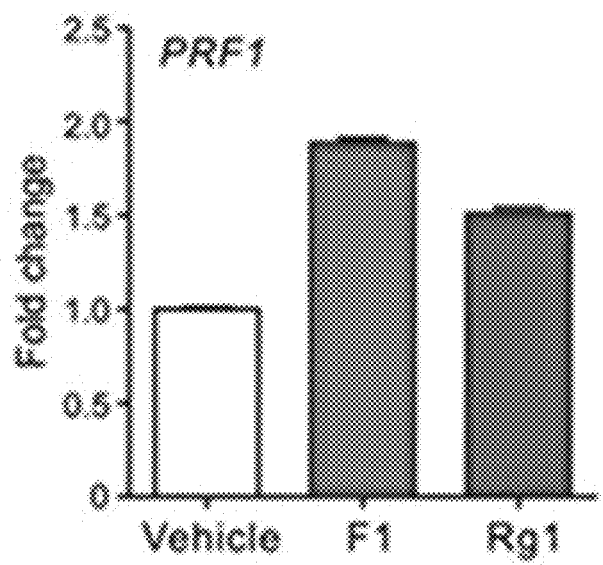
FIG. 6a is a graph showing a comparison of perforin (PRF1) expression levels of natural killer cells by treatment with ginsenoside F1 or ginsenoside Rg1.
Figure 6B:
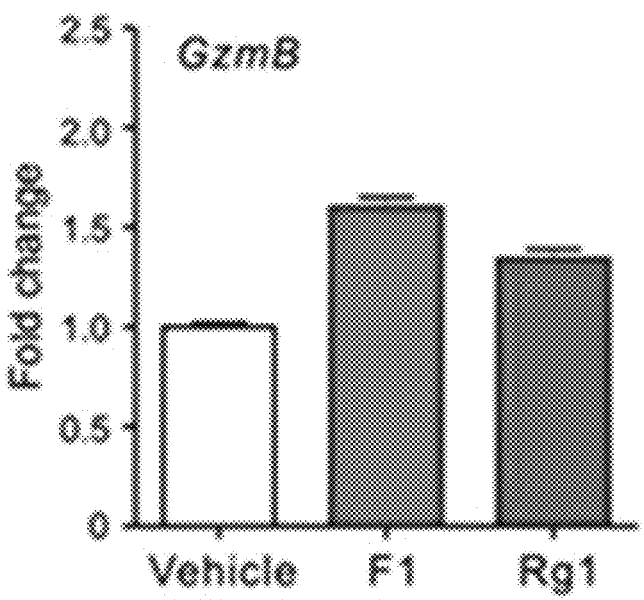
FIG. 6b is a graph showing a comparison of granzyme B (GzmB) expression levels of natural killer cells by treatment with ginsenoside F1or ginsenoside Rg1.

As a result, all ginsenoside-treated groups showed increased expressions of perforin and granzyme B. Specifically, a ginsenoside F1-treated group showed about 2 times higher expression level of perforin, compared to a non-treated group, and also a high expression level of perforin, compared to a ginsenoside Rg1-treated group (FIG. 6a). Further, the ginsenoside F1-treated group showed about 1.5 times higher expression level of granzyme B, compared to the non-treated group, and also a high expression level of granzyme B, compared to a ginsenoside Rg1-treated group (FIG. 6b). Accordingly, it was confirmed that ginsenoside F1 exhibits excellent immune enhancing effects, compared to ginsenoside Rg1.

EXAMPLE 6

In Vivo Natural Killer Cell-Based Immune Enhancement Activity of Ginsenoside F1

To evaluate effectiveness of in vivo cell-killing activity of ginsenoside F1, natural killer cell-sensitive RMA-S (MHC class I$^-$) and natural killer cell-resistant RMA (MHC class I$^+$) target cell systems were used.

In detail, mice were pretreated with ginsenoside F1 at a dose of 25 mg/kg. A mixture of RMA-S/RMA cells, each cell labeled with different fluorescence intensity, was administered into the mice via intraperitoneal injection. 8 hours later, a selective reduction rate of RMA-S by natural killer cells was analyzed by FACS.

Figure 7:
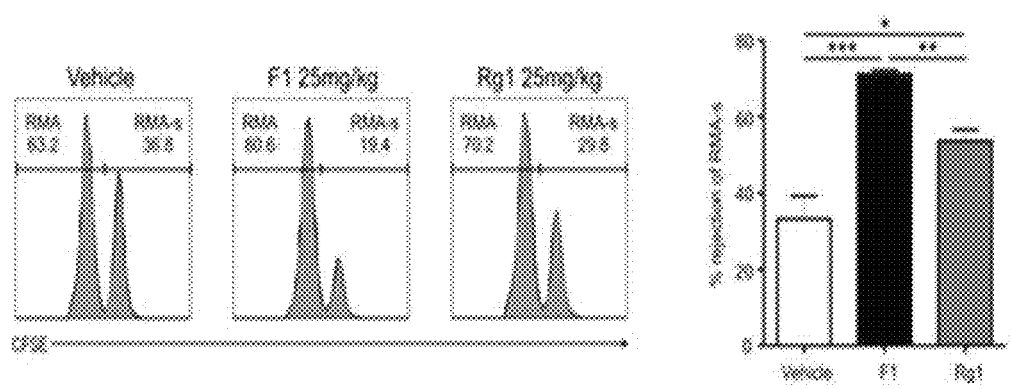
FIG. 7 is a graph showing a comparison of selective reduction rates of RMA-S in mice which were administered with RMA-S and RMA cells via intraperitoneal injection, after pretreatment of ginsenoside F1 or ginsenoside Rg1.

As a result, all ginsenoside-treated groups showed selectively reductions of RMA-S. In detail, a ginsenoside F1-treated group showed about 70% or more removability, whereas a non-treated group vehicle) showed about 35% removability, indicating that the RMA-S reduction effect of the ginsenoside F1-treated group was 2 times higher than that of the non-treated group. It was also confirmed that a group treated with an equal amount of ginsenoside Rg1 showed about 52% removability (FIG. 7). Accordingly, it was confirmed that ginsenoside F1 exhibits excellent immune enhancing effects in vivo, and in particular, ginsenoside F1 exhibits higher immune enhancing effects, compared to ginsenoside Rg1.

Based on the above description, it will be understood by those skilled in the art that the present invention may be implemented in a different specific form without changing the technical ideas or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

What is claimed is:

1. A method for enhancing innate immunity in a subject selected based on a need for enhanced innate immunity, comprising administering composition comprising ginsenoside F1 as an active ingredient, thereby enhancing innate immunity.

2. The method claim 1, wherein composition further comprises ginsenoside Rg3.

3. The method of claim 2, wherein the composition comprises ginsenoside F1 and ginsenoside Rg3 at a weight ratio of 1:0.1 to 1:1.

4. The method of claim 1, wherein the innate immunity is provided by innate immune cells selected from the group consisting of natural killer cells (NK cells), immune cells, peripheral blood mononuclear cells (PBMCs), and dendritic cells.

5. The method of claim 1, wherein the composition promotes degranulation activity of natural killer cells (NK cells).

6. The method of claim 1, wherein the composition promotes cell-killing activity of natural killer cells (NK cells).

7. The method of claim 1, wherein the composition increases expressions of a cell-killing factor of natural killer cells (NK cells).

8. The method of claim 7, wherein the cell-killing factor of NK cells is perforin or granzyme.

* * * * *